(12) United States Patent
Maruyama et al.

(10) Patent No.: US 9,193,654 B2
(45) Date of Patent: Nov. 24, 2015

(54) COSMETIC BASES AND COSMETICS CONTAINING THE SAME

(75) Inventors: Kei-ichi Maruyama, Kawasaki (JP); Yoji Tezuka, Kawasaki (JP)

(73) Assignee: NOF CORPORATION, Tokyo (JP)

(*) Notice: Subject to any disclaimer, the term of this patent is extended or adjusted under 35 U.S.C. 154(b) by 1606 days.

(21) Appl. No.: 11/664,512

(22) PCT Filed: Oct. 6, 2005

(86) PCT No.: PCT/JP2005/018826
§ 371 (c)(1),
(2), (4) Date: May 31, 2007

(87) PCT Pub. No.: WO2006/038724
PCT Pub. Date: Apr. 13, 2006

(65) Prior Publication Data
US 2007/0280897 A1    Dec. 6, 2007

(30) Foreign Application Priority Data
Oct. 6, 2004   (JP) ................. 2004-294204

(51) Int. Cl.
| | |
|---|---|
| *A61K 8/00* | (2006.01) |
| *A61K 8/30* | (2006.01) |
| *A61K 8/34* | (2006.01) |
| *A61K 8/39* | (2006.01) |
| *C07C 43/11* | (2006.01) |
| *A61K 8/86* | (2006.01) |
| *A61K 8/90* | (2006.01) |
| *A61Q 19/00* | (2006.01) |

(52) U.S. Cl.
CPC . *C07C 43/11* (2013.01); *A61K 8/86* (2013.01); *A61K 8/90* (2013.01); *A61Q 19/00* (2013.01); *A61Q 19/007* (2013.01)

(58) Field of Classification Search
CPC .......... A61K 8/86; A61K 8/90; A61Q 19/00; A61Q 19/007; C07C 43/11
See application file for complete search history.

(56) References Cited

U.S. PATENT DOCUMENTS

| | | | | |
|---|---|---|---|---|
| 4,200,733 | A | * | 4/1980 | Perner et al. ................... 528/417 |
| 4,476,107 | A | * | 10/1984 | Schmolka ........................ 424/49 |
| 4,597,975 | A | * | 7/1986 | Woodward et al. ............ 424/672 |
| 4,636,525 | A | * | 1/1987 | Ochiai et al. ................... 514/786 |
| 4,703,114 | A | * | 10/1987 | Mori et al. ...................... 536/4.1 |
| 4,745,170 | A | | 5/1988 | Bushman et al. |
| 4,985,047 | A | | 1/1991 | Sung et al. |
| 5,003,111 | A | * | 3/1991 | Harper ............................ 568/618 |
| 5,131,921 | A | | 7/1992 | Sung et al. |
| 5,211,721 | A | | 5/1993 | Sung et al. |
| 5,237,036 | A | * | 8/1993 | Spitzer ............................ 528/67 |
| 5,246,977 | A | * | 9/1993 | Mussini .......................... 521/159 |
| 5,429,820 | A | * | 7/1995 | Kamitani et al. .............. 424/401 |
| 5,490,978 | A | * | 2/1996 | Spaltro et al. .................... 424/49 |
| 5,709,852 | A | * | 1/1998 | Gopalkrishnan et al. .. 424/78.08 |
| 5,720,800 | A | * | 2/1998 | Matsumoto ........................ 106/2 |
| 6,103,850 | A | * | 8/2000 | Reichel et al. .................. 528/60 |
| 6,335,001 | B1 | * | 1/2002 | Palkrishnan et al. ........... 424/49 |
| 6,335,311 | B1 | * | 1/2002 | Namiki et al. ................. 508/579 |
| 6,410,676 | B1 | | 6/2002 | Yamasaki et al. |
| 2003/0180335 | A1 | * | 9/2003 | Ohmori et al. ................ 424/401 |
| 2005/0079188 | A1 | | 4/2005 | Ohmori et al. |

FOREIGN PATENT DOCUMENTS

| | | | |
|---|---|---|---|
| EP | 0 444 770 B1 | | 9/1991 |
| EP | 1 041 100 A1 | | 10/2000 |
| EP | 1 437 118 A1 | | 7/2004 |
| GB | 722 746 | * | 1/1955 |
| GB | 917951 | * | 2/1963 |
| JP | A-52-69881 | | 6/1977 |
| JP | A-4-270744 | | 9/1992 |
| JP | A-06-041581 | | 2/1994 |
| JP | A 6-56648 | | 3/1994 |
| JP | A-8-59818 | | 3/1996 |
| JP | A-9-157135 | | 6/1997 |
| JP | A 10-167948 | | 6/1998 |
| JP | A 2000-96075 | | 4/2000 |

(Continued)

OTHER PUBLICATIONS

Ikeda, Taichi; Lee, Won Kyu; Ooya, Tooru; Yui, Nobuhiko; "Thermodynamic Analysis of Inclusion Complexation Between α-Cyclodextrin-Based Molecular Tube and Poly(ethylene oxide)-block-poly(tetrahydrofuran)-block-poly(ethylene oxide) Triblock Copolymer," 2002, ACS, Journal of Physical Chemistry B, vol. 107, No. 1, pp. 14-19.*

(Continued)

*Primary Examiner* — Suzanne Ziska
*Assistant Examiner* — Ivan Greene
(74) *Attorney, Agent, or Firm* — Oliff PLC

(57) ABSTRACT

Cosmetic bases consisting of alkylene oxide derivatives represented by the general formula (I): Z—$\{O(AO)_l(EO)_m$—$(BO)_nH\}_a$(I) wherein Z is a residue derived from a compound having three to nine hydroxyl groups by the removal of the hydroxyl groups; a is 3 to 9; AO is $C_{3-4}$ oxyalkylone; EO is oxyethylene; l and m represent the average numbers of added $C_{3-4}$ oxyalkylene molecules and oxyalkylene molecules respectively and satisfy the relationships: $1 \leq l \leq 50$ and $1 \leq m \leq 50$ respectively; the AO/EO weight ratio is 1/5 to 5/1 and AO's and EO's may be added at random or in block; BO is oxyalkylene having 4 carbon atoms; and n represents the average number of added BO molecules and satisfies the relationship: $0.5 \leq n \leq 5$.

17 Claims, No Drawings

(56) References Cited

FOREIGN PATENT DOCUMENTS

| | | | |
|---|---|---|---|
| JP | A-2000-154161 | | 6/2000 |
| JP | 2000-309632 A1 | * | 11/2000 |
| JP | 2000309632 A1 | * | 11/2000 |
| JP | A 2000-309632 | | 11/2000 |
| JP | A 2000-325771 | | 11/2000 |
| JP | A 2001-2591 | | 1/2001 |
| JP | A 2002-87928 | | 3/2002 |
| JP | A 2003-12442 | | 1/2003 |
| JP | A 2003-113023 | | 4/2003 |
| JP | A 2004-18610 | | 1/2004 |
| JP | A 2004-67607 | | 3/2004 |
| JP | 2004-300099 A1 | * | 10/2004 |
| JP | A 2004-300099 | | 10/2004 |
| WO | WO 90/14327 | * | 11/1990 |
| WO | WO 9833833 A1 | * | 8/1998 |

OTHER PUBLICATIONS

Solodov, V. A.; Varnayskaya, O. A.; Khvatova L. K.; Fakhrutdinov, B. R.; Lebedev, N. A.; Diyarov, I. N.; "Sorbitol-Based Demulsifying Agents and Their Surfactant Properties," 2005, Pleiades Publishing inc.; Russian Journal of Applied Chemistry, vol. 78, No. 6, pp. 944-949.*

Robinson, I. M.; Pechhold, E.; Pruckmayr G.; "Polyether Glycols from Tetrahydrofuran and Ethylene Oxide," 1981, ACS, ACS Symposium Series, vol. 172, Chapter 15, pp. 197-203.*

Mimasaka, Nanba, et al.; English Language translation of Japaneses Patent document JP-2000-309632; Translated by FLS, Inc., Apr. 2010; pp. 1-16.*

Hawley's Condensed Chemical Dictionary entry for "polyol," p. 1016.*

Merriam-Webster's Collegiate Dictionary, 11$^{th}$ ed., 2003; entry for "derivative," p. 336.*

Misaka, Ishida; Machine English Language translation, as filed by applicants on Jun. 18, 2007, pp. 1-10.*

Lambers, H. et al.; "Natural skin surface pH is on average below 5, which is beneficial for its resident flora," 2006, (PMID: 18489300) International Journal of Cosmetic Science, vol. 28, No. 5, abstract only, p. 1 (as provided).*

English Language translation of JP-2004-300099-A1, translated by Schreiber Translations, Inc., Apr. 2010, pp. 1-33.*

Iwadare et al., "Hydrophilic detergents for contact lenses," XP-002459596.

Rawlings et al., "Skin Moisturization," 2002. XP-002459595, p. 248-249.

Oct. 26, 2010 Japanese Office Action issued in Japanese Patent Application No. 2006-539357 (with translation).

* cited by examiner

COSMETIC BASES AND COSMETICS CONTAINING THE SAME

TECHNICAL FIELD OF THE INVENTION

The present invention concerns a basic agent for use in cosmetics having both excellent feel and moisturizing effect, and cosmetics blended therewith.

BACKGROUND ART

Humectants have become essential for cosmetics and there is a tendency to favor those having high moist and refreshing feel in view of the recent trend of consumers. However, humectants and cosmetics capable of coping with such demands have not sufficiently been obtained yet.

For example, while watersoluble polyhydric alcohols typically represented by glycerin, polypropylene glycol and 1,3-butylene glycol have excellent moist feel, sticky feel in noted when blending them at a high concentration. When blending triglyceride or silicone oil, etc. intending to provide smooth feel, since there is no compatibility between both of then, a great amount of an emulsifier is necessary, which lowers the smooth feel or moist feel.

In view of the above, for providing properties of both of moist and smooth feel with a water soluble basic agent, while cosmetics blended with N-acetyl basic amino acid (for example, in Japanese Patent publication No. 2002-87928A), poly-γ-glutamic acid crosslinked polymer (or example, in Japanese Patent publication No. 2003-12442A, or PEG dialkyl ether (for example, in Japanese Patent publication No. 10-167948A) have been reported, none of them have yet provided a sufficient effect at present.

Further, in a case of egg cosmetics for moisture retention, they became dry when an applied portion is washed away with a soap or the like, and it is necessary to compensate for the loss of moist skin feel, for example, by re-applying another moisturizing cosmetic such as cream.

While Japanese Patent publication No. 2003-113023A discloses skin cosmetics comprising an alkylene aside derivative, the state after wading away the applied portion with a soap or the like has not yet been studied.

DISCLOSURE OF THE INVENTION

An object of the present invention is to provide a basic agent for use in cosmetics having both excellent feel and moisturizing effect, while keeping moisture even after cleaning, as well as cosmetics blended therewith.

That is, the present invention is shown below:
(1) A basic agent for use in cosmetics, comprising an alkylene oxide derivative represented by the following formula (I):

$$Z-\{O(AO)_p(EO)_m-(BO)_nH\}_a \quad (I)$$

(where Z represents a residue of a compound having 3 to 9 hydroxyl groups with the hydroxyl groups removed, a is from 3 to 9, AO represents an oxyalkylene group of 3 to 4 carbon atoms, EO represents oxyethylene group, p and m each represents an average additional mol number of the oxyalkylene groups of 3 to 4 carbon atoms and the oxyethylene groups, respectively, and $\leq_p \leq 50$, $1 \leq_m \leq 50$, the weight ratio (AO/EO) of AO to EO is from 1/5 to 5/1, AO and E0 may be added in a random form or may be added in a block form. BO represents an oxyalkylene group with a number of carbon atoms of 4, and n is an average additional mol number thereof, which is: $0.5 \leq n \leq 5$).

(2) The basic agent for use in cosmetics in which AO and EO are added in a random form.
(3) The cosmetics blended with the basic agent for use in cosmetics.
(4) The cosmetics containing the basic agent for use in cosmetics by from 0.05 to 50% by weight and a water-soluble polyhydric alcohol by from 0.05 to 50% by weight The basic agent for use in cosmetics of the invention has both properties of excellent smooth and moist feel, good to the touch and providing most Effective performance when blended in the cosmetics.

BEST MODES FOR CARRYING OUT THE INVENTION

In the alkylene oxide derivative shown by the formula (I), Z represents a residue of a compound having 3 to 9 hydroxyl groups with the hydroxyl groups removed, and a is a number of the hydroxyl groups of the compound Z, which is from 3 to 9. The compound having from 3 to 9 hydroxyl groups includes, for example, glycerin and trimethylol propane for a=3, erythritol, pentaerythritol, sorbitan, alkyl glycoside, and diglycerin for a=4, xylytol for a=5, dipentaerythritol, sorbitol and inositol for a=6, sucrose and trehalose for a=8, maltitol for a=9, and mixtures thereof. Preferably, Z is a residue of a compound having 3 to 9 hydroxyl groups with the hydroxyl groups removed, which satisfies $3 \leq a \leq 6$. In a case where it is 2 or less, a sufficient moist feel cannot be obtained and, on the other hand, in a case where the number of functional groups is 10 or more, it results in sticky feel.

AO represents an oxyalkylene group of 3 to 4 carbon atoms and includes, for example, oxypropylene group, oxybutylene group, oxyisobutylene group, oxy-t-butylene group, oxytrimethylene group, and oxytetramethylene group. Preferred are oxypropylene group and oxybutylene group and more preferred is oxypropylene group.

p is an average additional mol number of AO, which is: $1 \leq p \leq 50$ and, preferably, $2 \leq p \leq 20$. m is an average additional mol number of EO, which is: $1 \leq m \leq 50$ and, preferably, $2 \leq m \leq 20$. In a case where AO is 0, it results in sticky feel and in a case where it exceeds 50, the moist feel is deteriorated. Further, in a case where EO is 0, the moist feel is deteriorated and in a case where it exceeds 50, it results in sticky feel.

The weight ratio (AO/EO) of AO to EO is from 1/5 to 5/1 and, preferably, from 1/4 to 4/1. In a case where it is less than 1/5, it results in sticky feel and, in a case, where it is more than 5/1, the moist feel is deteriorated.

The sequence of the addition of AO and EO is not particularly specified and they may be added in a block form or may be added in a random form. Preferably, they are added at random BO represents an oxyalkylene group with the number of carbon atoms of 4 and includes, for example, oxybutylene group, oxyisobutylene group, oxytetramethylene group, and oxy-t-butylene group. Oxybutylene group is preferred.

n is an average additional mol number of BO, which is $0.5 \leq n \leq 5$, preferably, $0.8 \leq n \leq 3$ and, more preferably, $1 \leq n \leq 3$. In a case where it is less than 0.5, it results in sticky feel and, in a case where it exceeds 5, the moist feel is deteriorates.

In the formula (1), it is necessary that (BO)n is bonded to a terminal hydrogen atom.

The alkylene oxide derivative shown by the formula (I) of the invention can be produced by a known method. For example, it can be obtained by addition polymerization of ethylene oxide and an alkylene oxide of 3 to 4 carbon atoms to a compound having three or more hydroxyl groups and then reacting an alkylene oxide with a number of carbon atoms of 4.

In the step of addition polymerization of ethylene oxide (EO) and an alkylene oxide (AO) 3 to 4 carbon atoms to the compound having three or more hydroxyl groups, EO and AO may be put to random polymerization or block polymerization. However, it is necessary that BO is reacted after the addition polymerization of EO and AO.

Further, the form of the cosmetics blended with the basic agent for use in the cosmetics of the invention is not particularly restricted, and it may include aqueous cosmetics, water-in-oil type or oil-in-water type emulsion cosmetics, or oily cosmetics. And it may be of forms such as shampoo, rinse, body soap, face washing agent, skin lotion, milky lotion, cam, hair conditioner, lipstick, and hair growing agent.

The blending amount of the basic agent for use in cosmetics in the cosmetics after the invention is not particularly restricted and usually it is Mended ranging from 0.01 to 70% by weight Further, by blending a water-soluble polyhydric alcohol as cosmetics, both the feel and the moisturizing effect are further improved. A combination comprising preferably from 0.05 to 50% by weight of the basic agent of the invention and from 0.05 to 50% of the water-soluble polyhydric alcohol, more preferably, from 0.1 to 25% by weight of the basic agent of the invention and from 0.1 to 25% by weight uf the water-soluble polyhydric alcohdl, and, further preferably, from 1 to 10% by weight of the basic agent of the invention and from 1 to 10% by weight of the watersoluble polyhydic alcohol is more effective.

The water-soluble polyhydric alcohol is a water-soluble compound having two or more hydroxyl groups in the molecule and includes, for example, propylene glycol, dipropylene glycol, isoprene glycol, 1,3-butylene glycol glycerin, diglycerin, polyethylene glycol, sorbitol, maltitol, methyl glucoside, alkyl glucoside, and alkylene oxide adducts thereof. Among them, dipropylene glycol, iropropylene glycol, 1,3-butylene glycol, glycol, diglycerin, polyethylene glycol, methyl glycoside, and ethylene oxide adducts thereof are preferred.

In cosmetics of the invention, other ingredients may also be contained within a range that does not deteriorate the performance of the invention. For example, they include lower alcohols, hydrocarbon oils, natural oils and fats, synthetic triglycerides, aster ails, waxes, silicone derivatives, oily basic agents, anionic surfactants, amphoteric surfactants, nonionic surfactants, cationic surfactants, semi-polar surfactants, water-soluble high molecular materials, organic or inorganic salts, pH adjusting agents, sterilizers, chelating agents, antioxidants, UV-ray absorbents, vitamins, natural extracts derived from animal and plants, dyes, pigments, and perfumes.

EXAMPLES

Synthesis Example 1

[Synthesis of polyoxybutylene (10 mol) polyoxyethylene (20 mol) polyoxypropylene (20 mol) sorbitol ether (polyoxyethylene and polyoxypropylene form block polymer)]

12 g of potassium hydroxide as a cat along with 182 g of sorbitol was charged into an autoclave and, after replacing air in the autoclave with dry nitrogen, the catalyst was completely dissolved at 140° C. under stirring. Then, 1160 g of propylene oxide was dropped by a dropping device and stirred for 2 hours. Successively, 880 g of ethylene aide was dropped by the dropping device and stirred for 2 hours. Further, 720 g of butylene oxide was dropped by the dropping device and reacted under stirring for 2 hours. Then, the on composition was taken out of the autoclave, neutralized with hydrogen chloride to pH 6-7, and treated for removing the contained water at a reduced pressure of 0.095 MPa (gage pressure, at 100° C. for one hour. Further, filtration was conducted to remove the salt formed after the treatment to obtain a basin agent as Compound 1.

Synthesis Example 2

[Synthesis of polyoxybutylene (5 mol), polyoxyethylene (10 mol), polyoxopropylene (10 mol), glycerin ether (polyoxyethylene and polyoxypropylene form random polymer)]

6 g of potassium hydroxide as a catalyst along with 92 g of glycerin was charged into an autoclave and, after replacing air in the autoclave with dry nitrogen, the catalyst was completely dissolved at 140° C. under stirring. Then, a mixture of 440 g of ethylene wide and 680 g of propylene oxide was dropped by a dropping device and stirred for 2 hour. Further, 360 g of butylene oxide was dropped by the dropping device and reacted under stirring for 2 hours. Then, a reaction composition was taken out of the autoclave, neutralized with hydrogen chloride to pH 6-7, and treated for removing the contained water at a reduced pressure of 0.095 MPa (gage pressure), at 100° C. for one hour. Further, filtration was conducted to remove the salt formed after the treatment to obtain a basic agent as Compound 2.

Synthesis Examples 3 to 11

In the same manner as in the Synthesis Example 1 or Synthesis Example 2, synthesis of compounds shown in Table 1 was conducted.

TABLE 1

|   |   | Compound | Z | a | p | m | n | EO/PO | Absence of stiky feel | Moist feel |
|---|---|---|---|---|---|---|---|---|---|---|
| EXAMPLE | 1 | 1 | Sorbitol | 6 | 3.3 | 3.3 | 1.7 | 1.3/1 | 36 | 38 |
|  | 2 | 2 | Glycerin | 3 | 3.3 | 3.3 | 1.7 | 1.3/1 | 47 | 46 |
|  | 3 | 3 | Sucrose | 8 | 6.3 | 6.3 | 1.9 | 1.3/1 | 37 | 43 |
|  | 4 | 4 | Glycerin | 3 | 1.7 | 6 | 1.7 | 1/4.7 | 36 | 43 |
|  | 5 | 5 | Glycerin | 3 | 6 | 1.7 | 1.7 | 4.6/1 | 44 | 35 |
|  | 6 | 6 | Sorbitol | 6 | 5 | 5 | 4 | 1.3/1 | 45 | 38 |
|  | 7 | Compound 2:glycerin = 50:50 | — | — | — | — | — | — | 47 | 48 |
| COMPARATIVE EXAMPLE | 1 | 7 | Sorbitol | 6 | 5 | 5 | 0 | 1.3/1 | 33 | 42 |
|  | 2 | 8 | Glycerin | 3 | 6.7 | 0 | 0 | 1/0 | 23 | 41 |
|  | 3 | 9 | Glycerin | 3 | 0 | 6.7 | 0 | 0/1 | 43 | 24 |
|  | 4 | 10 | C6H13O(EO)6C6H13 |  |  |  |  | 1/0 | 40 | 32 |
|  | 5 | Glycerin | — |  | 3 | — | — | — | 15 | 45 |

TABLE 1-continued

|   | Compound | Z | a | p | m | n | EO/PO | Absence of stiky feel | Moist feel |
|---|----------|---|---|---|---|---|-------|----------------------|------------|
| 6 | Propylene glycol | — | 2 | — | — | — | — | 18 | 42 |
| 7 | Polyethylene glycol (molecular weight 300) | — | 2 | 7 | 0 | 0 | 1/0 | 21 | 39 |
| 8 | Lysine hydrogen chloride | — | — | — | — | — | — | 17 | 41 |

Examples 1 to 7 and Comparative Examples 1 to 8

Tests shown below were conducted using each of basic agents for use in the cosmetics. Results are shown in Table 1.Each of the blending amounts is based on the weight percentage.
(Functional Evaluation)

An aqueous 10 wt % solution of each conpound was prepared and evaluation was made for the moist feel and absence of stickiness (smooth feel) by 10 expert panellers. As the evaluation method, a sample was applied after cleaning the upper arm and a total value of the evaluation in five ranks for the moist feel and absence of sticky feel from just al to 30 min after application was adopted. It was judged favorable for those with scores of 35 or higher.
<Absence of Sticky Feel (Smooth Feel)>

5: Spreading is excellent, with an extremely light feel with no resistance felt when rubbed on the skin 4: Spreading is good, with a light feel without any resistance felt when rubbed on the skin 3: Spreading is somewhat poor, with a slight resistance felt when rubbed on the skin 2: Spreading is poor, with heavy resistance felt when rubbed on the skin 1: Spreading is extremely poor, with an extremely heavy resistance felt when rubbed on the skin
<Moist Feel>

5: No dryness at all, with sufficient mist feel

4: No dryness with moist feel

3: Some dryness with somewhat insufficient moist feel

2: Dryness with insufficient moist fed

1: Considerable dryness with extremely insufficient moist feel

The basic agent of the invention satisfies the sores both for the moist feel and absence of stickiness. However, Comparative Examples 1 to 8 can not satisfy the two properties simultaneous.

Examples 8 to 17 and Comparative Examples 9 to 15

The compounds 1 to 10, glycerin, sorbitol, polyethylene glycol (molecular weight: 300) and lysine hydrogen chloride were blended to aqueous phase portion. Oil phase portion having the following composition in the basic agent was heated to 80° C. to dissolve uniformly, and the aqueous phase portion was gradually added thereto and stirred at the same temperature. They were then cooled to 40° C. to form lotion and the same evaluation items as in Example 1 was conducted The results are shown in Table 2.

| Oil phase portion | |
|---|---|
| Behenyl alcohol | 2.0 wt % |
| Squalane | 6.0 wt % |
| Isopropyl millistate | 0.5 wt % |
| Sorbitan monostearate | 1.0 wt % |
| Glycerin monostearate | 1.0 wt % |
| Polyoxyethylene (20 mol) dodecyl ether | 1.5 wt % |
| Perfume | approximate amount |
| Preservatives | approximate amount |
| Aqueous phase portion | |
| Humectant | Refer to Table 3 |
| Purified water | balance (to make-up the entire portion to 100) |

For the prepared lotion, evaluation was conducted by the method described above for the moist feel and absence of sticky feel (smooth fed), and evaluation after cleaning was conducted by the following method.
(Evaluation After Cleaning)

After conducting a functional evaluation for the formulated product described above by 10 expert panellers, total value for evaluation in five ranks for the feeling 15 min after cleaning the upper arm portion with the soap was adopted. Those with scores of 35 or higher were judged favorable.
<Feel After Cleaning>

5: Almost fee from sin dryness, with moist feel

4: No skin dryness, with somewhat moist feel

3: A little skin dryness, but not reaching a feel of skin roughness

2: A little more skin dryness, with a feel approaching that of in roughness

1: Extreme skin dryness with feel of skin roughness

TABLE 2

| Humectant blend | Examples | | | | | | | | | | Comparative Examples | | | | | | |
|---|---|---|---|---|---|---|---|---|---|---|---|---|---|---|---|---|---|
| (Wt. %) | 8 | 9 | 10 | 11 | 12 | 13 | 14 | 15 | 16 | 17 | 9 | 10 | 11 | 12 | 13 | 14 | 15 |
| Compound 1 | 20 | — | — | — | — | — | — | — | — | — | — | — | — | — | — | — | — |
| Compound 2 | — | 20 | — | — | — | — | 10 | 10 | 5 | 15 | — | — | — | — | — | — | — |
| Compound 3 | — | — | 20 | — | — | — | — | — | — | — | — | — | — | — | — | — | — |
| Compound 4 | — | — | — | 20 | — | — | — | — | — | — | — | — | — | — | — | — | — |
| Compound 5 | — | — | — | — | 20 | — | — | — | — | — | — | — | — | — | — | — | — |
| Compound 6 | — | — | — | — | — | 20 | — | — | — | — | — | — | — | — | — | — | — |
| Compound 7 | — | — | — | — | — | — | — | — | — | — | 20 | — | — | — | — | — | — |
| Compound 8 | — | — | — | — | — | — | — | — | — | — | — | 20 | — | — | — | — | — |
| Compound 9 | — | — | — | — | — | — | — | — | — | — | — | — | 20 | — | — | — | — |

TABLE 2-continued

| Humectant blend (Wt. %) | Examples | | | | | | | | | | Comparative Examples | | | | | | |
|---|---|---|---|---|---|---|---|---|---|---|---|---|---|---|---|---|---|
| | 8 | 9 | 10 | 11 | 12 | 13 | 14 | 15 | 16 | 17 | 9 | 10 | 11 | 12 | 13 | 14 | 15 |
| Compound 10 | — | — | — | — | — | — | — | — | — | — | — | — | — | 20 | — | — | — |
| Glycerin | — | — | — | — | — | — | 10 | — | 15 | 5 | — | — | — | — | 20 | — | 10 |
| Sorbitol | — | — | — | — | — | — | — | 10 | — | — | — | — | — | — | — | 10 | — |
| Polyethylene glycol (MW: 300) | — | — | — | — | — | — | — | — | — | — | — | — | — | — | — | 10 | — |
| Lysine hydrogen | — | — | — | — | — | — | — | — | — | — | — | — | — | — | — | — | 10 |
| Absence of sticky feel | 36 | 44 | 36 | 35 | 45 | 44 | 47 | 46 | 44 | 47 | 30 | 20 | 45 | 40 | 13 | 15 | 12 |
| Moist feel | 37 | 43 | 44 | 43 | 38 | 37 | 48 | 47 | 48 | 44 | 40 | 39 | 22 | 30 | 46 | 45 | 42 |
| Feel after cleaning | 37 | 41 | 40 | 38 | 35 | 35 | 43 | 42 | 40 | 39 | 29 | 24 | 16 | 23 | 30 | 35 | 28 |

In the same manner, as in the results of evaluation items for the basic agents per se, cosmetics of the invention sat all of the absence of sticky feel, moist feel, and feel after cleaning in view of Examples 8 to 17. However, none of Comparative Examples 9 to 15 simultaneously satisfies the three properties.

The invention claimed is:

1. A skin cosmetic comprising an aqueous cosmetic, a water-in-oil type emulsion cosmetic, an oil-in-water type emulsion cosmetic, or an oily cosmetic comprising an oil, the skin cosmetic comprising:
   a basic agent, the basic agent being present in an amount of from 0.05 to 50 weight percent of the total weight of the skin cosmetic; and
   a water-soluble polyhydric alcohol, the water-soluble polyhydric alcohol being present an amount of from 0.05 to 50 weight percent of the total weight of the skin cosmetic; wherein
   the basic agent is represented by the following formula (I):

$$Z—\{O(AO)_p(EO)_m—(BO)_nH\}_a \qquad (I),$$

where
   Z represents a residue that is obtained by a process during which hydroxyl groups of a compound selected from the group consisting of glycerin, trimethylol propane, erythritol, pentaerythritol, sorbitan, alkyl glycoside, diglycerin, xylytol, dipentaerythritol, sorbitol, inositol, sucrose, trehalose and maltitol, are removed, and replaced with —$\{O(AO)_p(EO)_m—(BO)_nH\}_a$,
   a is an integer selected from the group consisting of 3, 4, 5, 6, 8, and 9,
   AO represents an oxypropylene group,
   EO represents an oxyethylene group,
   p and m represent average addition mol numbers of said oxypropylene group and said oxyethylene group, respectively, $1 \leq p \leq 50$, and $1 \leq m \leq 50$,
   a weight ratio of AO to EO is in a range of from 1/5 to 5/1,
   AO and EO form random or block copolymers,
   BO represents an oxybutylene group bonded to the terminal hydrogen atom, and
   n is an average mol number, and $0.5 \leq n \leq 5$, and
     wherein the skin cosmetic is a shampoo, a rinse, a body soap, a face washing agent, a skin lotion, a milky lotion, a cream, a hair conditioner, a lipstick, or a hair growing agent.

2. The skin cosmetic of claim 1, wherein AO and EO form random copolymers.

3. The skin cosmetic of claim 1, wherein said compound from which the residue represented by Z is obtained from is selected from the group consisting of glycerin, trimethylol propane, erythritol, pentaerythritol, sorbitan, alkyl glycoside, diglycerin, xylytol, dipentaerythritol, sorbitan, inositol, sucrose, and trehalose, and
   a is an integer selected from the group consisting of 3, 4, 5, 6, and 8.

4. The skip cosmetic of claim 1, wherein p satisfies $2 \leq p \leq 20$.

5. The skin cosmetic of claim 1, wherein m satisfies $2 \leq m \leq 20$.

6. The skin cosmetic of claim 1, wherein said water-soluble polyhydric alcohol is selected from the group consisting of propylene glycol, glycerin, sorbitol and maltitol.

7. The skin cosmetic of claim 1, wherein the oxybutylene group is derived from butylene oxide.

8. The skin cosmetic of claim 1, wherein the skin cosmetic comprises a water-in-oil type emulsion cosmetic or an oil-in-water type emulsion cosmetic.

9. The skin cosmetic of claim 1, wherein the skin cosmetic prevents a sticky feel on skin, and provides moisture feel on skin.

10. The skin cosmetic of claim 1, further comprising an ester oil.

11. The skin cosmetic of claim 1, further comprising a lower alcohol.

12. The skin cosmetic of claim 1, wherein the skin cosmetic is a body soap, a face washing agent, a skin lotion, or a lipstick.

13. The skin cosmetic of claim 1, wherein the skin cosmetic is a skin lotion, or a lipstick.

14. The skin cosmetic of claim 1, wherein the skin cosmetic is a lipstick.

15. The skin cosmetic of claim 1, wherein the skin cosmetic is a skin lotion.

16. The skin cosmetic of claim 1, wherein the skin cosmetic is a shampoo, a hair conditioner, or a hair growing agent.

17. A cosmetic comprising:
   a basic agent, the basic agent being present in an amount of from 0.05 to 50 weight percent of the total weight of the skin cosmetic; and
   a water-soluble polyhydric alcohol, the water-soluble polyhydric alcohol being present in an amount of from 0.05 to 50 weight percent of the total weight of the skin cosmetic; wherein
   the basic agent is represented by the following formula (I):

$$Z—\{O(AO)_p(EO)_m—(BO)_nH\}_a \qquad (I),$$

where Z represents a residue that is obtained by a process during which hydroxyl groups of a compound selected from the group consisting of glycerin, trimethylol propane, erythritol, pentaerythritol, sorbitan, alkyl glycoside, diglycerin, xylytol, dipentaerythritol, sorbitol, inositol, sucrose, trehalose and maltitol, are removed, and replaced by $-\{O(AO)_p(EO)_m-(BO)_nH\}_a$, a is an integer selected from the group consisting of 3, 4, 5, 6, 8, and 9, AO represents an oxypropylene group, EO represents an oxyethylene group, p and m represent average addition mol numbers of said oxypropylene group and said oxyethylene group, respectively, $1 \leq p \leq 50$, and $1 \leq m \leq 50$, a weight ratio of AO to EO is in a range of from 1/5 to 5/1, AO and EO form random or block copolymers, BO represents an oxybutylene group bonded to the terminal hydrogen atom, and n is an average mol number, and $0.5 \leq n \leq 5$; wherein said cosmetic is a body soap, a face washing agent, a skin lotion, or a lipstick.

* * * * *